(12) United States Patent
Zhang et al.

(10) Patent No.: US 11,655,255 B2
(45) Date of Patent: May 23, 2023

(54) METHOD FOR CATALYTIC ASYMMETRIC SYNTHESIS OF PHOSPHORUS-STEREOGENIC (P-STEREOGENIC) NUCLEOSIDE DERIVATIVE AND CATALYST USED THEREIN

(71) Applicants: SPH NO.1 BIOCHEMICAL & PHARMACEUTICAL CO.,LTD., Shanghai (CN); Shanghai Jiaotong University, Shanghai (CN)

(72) Inventors: Wanbin Zhang, Shanghai (CN); Mo Wang, Shanghai (CN); Lu Zhang, Shanghai (CN); Xiaohong Huo, Shanghai (CN); Zhenfeng Zhang, Shanghai (CN); Qianjia Yuan, Shanghai (CN); Jianzhong Chen, Shanghai (CN)

(73) Assignees: SPH NO.1 BIOCHEMICAL & PHARMACEUTICAL CO., LTD., Shanghai (CN); Shanghai Jiaotong University, Shanghai (CN)

( * ) Notice: Subject to any disclaimer, the term of this patent is extended or adjusted under 35 U.S.C. 154(b) by 0 days.

(21) Appl. No.: 17/967,117

(22) Filed: Oct. 17, 2022

(65) Prior Publication Data
US 2023/0085986 A1    Mar. 23, 2023

(51) Int. Cl.
C07D 487/04    (2006.01)
(52) U.S. Cl.
CPC .................. *C07D 487/04* (2013.01)
(58) Field of Classification Search
None
See application file for complete search history.

(56) References Cited

U.S. PATENT DOCUMENTS

| | | | |
|---|---|---|---|
| 2016/0122374 A1 | 5/2016 | Chun et al. | |
| 2017/0071964 A1 | 3/2017 | Clarke et al. | |

FOREIGN PATENT DOCUMENTS

| | | |
|---|---|---|
| CN | 107073005 A | 8/2017 |
| CN | 111116656 A | 5/2020 |
| WO | 2017184668 A1 | 10/2017 |

OTHER PUBLICATIONS

Wang et al, Angew. Chem. Int. Ed., 59, 20814-20819 (Year: 2020).*
DiRocco, Daniel A. et al., A multifunctional catalyst that stereoselectively assembles prodrugs. Science, 2017, 356, 426-430.
Warren, Travis K. et al., Therapeutic efficacy of the small molecule GS-5734 against Ebola virus in rhesus monkeys. Nature,2016, 531(7594), 381-385.
Siegel, Dustin et al., Discovery and Synthesis of a Phosphoramidate Prodrug of a Pyrrolo[2,1-f][triazin-4-amino] Adenine C-Nucleoside (GS-5734) for the Treatment of Ebola and Emerging Viruses. Journal of Medicinal Chemistry, 2017, 60(5), 1648-1661.

* cited by examiner

*Primary Examiner* — Zinna Northington Davis

(57) ABSTRACT

A method for catalytic asymmetric synthesis of a phosphorus-stereogenic (P-stereogenic) nucleoside derivative of formula (3) and a catalyst used therein. The P-stereogenic nucleoside derivative (3) can be hydrolyzed to obtain remdesivir. Specifically, a nucleoside and phosphoryl chloride are subjected to asymmetric reaction under the catalysis of a chiral bicyclic imidazole catalyst in the presence of a base to produce the P-stereogenic nucleoside derivative of formula (3)

(3)

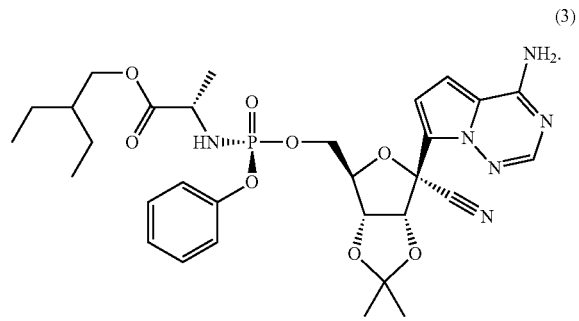

7 Claims, No Drawings

METHOD FOR CATALYTIC ASYMMETRIC SYNTHESIS OF PHOSPHORUS-STEREOGENIC (P-STEREOGENIC) NUCLEOSIDE DERIVATIVE AND CATALYST USED THEREIN

TECHNICAL FIELD

This application relates to pharmaceutical and chemical industry, particularly to a method for catalytic asymmetric synthesis of a key intermediate-phosphorus-stereogenic (P-stereogenic) nucleoside derivative in the synthesis of remdesivir and a catalyst used therein, and more particularly to a method for asymmetrically synthesizing the P-stereogenic nucleoside derivative through reaction of a nucleoside and phosphoryl chloride under the catalysis of a chiral bicyclic imidazole catalyst and in the presence of a base.

BACKGROUND

Phosphorus-stereogenic (P-stereogenic) nucleoside derivative (3) ($C_{30}H_{39}N_6O_8P$) is a key intermediate in the preparation of Remdesivir, such that it is of extreme importance to develop efficient synthesis methods of the P-stereogenic nucleoside derivative (3). Therefore, the direct asymmetric synthesis of the P-stereogenic nucleoside derivative (3) through reaction between the nucleoside and phosphoryl chloride has a brilliant application prospect.

In the prior art (US patent publication No. 20160122374; Warren, T. K.; Jordan, R.; Lo, M. K.; Ray, A. S.; Mackman, R. L.; Soloveva, V.; Siegel, D.; Perron, M.; Bannister, R.; Hui, H. C.; Larson, N.; Strickley, R.; Wells, J.; Stuthman, K. S.; Van Tongeren, S. A.; Garza, N. L.; Donnelly, G.; Shurtleff, A. C.; Retterer, C. J.; Gharaibeh, D.; Zamani, R.; Kenny, T.; Eaton, B. P.; Grimes, E.; Welch, L. S.; Gomba, L.; Wilhelmsen, C. L.; Nichols, D. K.; Nuss, J. E.; Nagle, E. R.; Kugelman, J. R.; Palacios, G.; Doerffler, E.; Neville, S.; Carra, E.; Clarke, M. O.; Zhang, L.; Lew, W.; Ross, B.; Wang, Q.; Chun, K.; Wolfe, L.; Babusis, D.; Park, Y.; Stray, K. M.; Trancheva, I.; Feng, J. Y.; Barauskas, O.; Xu, Y.; Wong, P.; Braun, M. R.; Flint, M.; McMullan, L. K.; Chen, S.-S.; Fearns, R.; Swaminathan, S.; Mayers, D. L.; Spiropoulou, C. F.; Lee, W. A.; Nichol, S. T.; Cihlar, T.; Bavari, S., Therapeutic Efficacy of the Small Molecule GS-5734 against Ebola Virus in Rhesus Monkeys. Nature 2016, 531, 381-385; Siegel, D.; Hui, H. C.; Doerffler, E.; Clarke, M. O.; Chun, K.; Zhang, L.; Neville, S.; Carra, E.; Lew, W.; Ross, B.; Wang, Q.; Wolfe, L.; Jordan, R.; Soloveva, V.; Knox, J.; Perry, J.; Perron, M.; Stray, K. M.; Barauskas, O.; Feng, J. Y.; Xu, Y.; Lee, G.; Rheingold, A. L.; Ray, A. S.; Bannister, R.; Strickley, R.; Swaminathan, S.; Lee, W. A.; Bavari, S.; Cihlar, T.; Lo, M. K.; Warren, T. K.; Mackman, R. L., Discovery and Synthesis of a Phosphoramidate Prodrug of a Pyrrolo[2,1-f][triazin-4-amino] Adenine C-Nucleoside (GS-5734) for the Treatment of Ebola and Emerging Viruses. Journal of Medicinal Chemistry 2017, 60, 1648-1661; WO 2017184668 and US patent publication No. 20170071964), the P-stereogenic nucleoside derivative (3) is synthesized indirectly, through the following scheme:

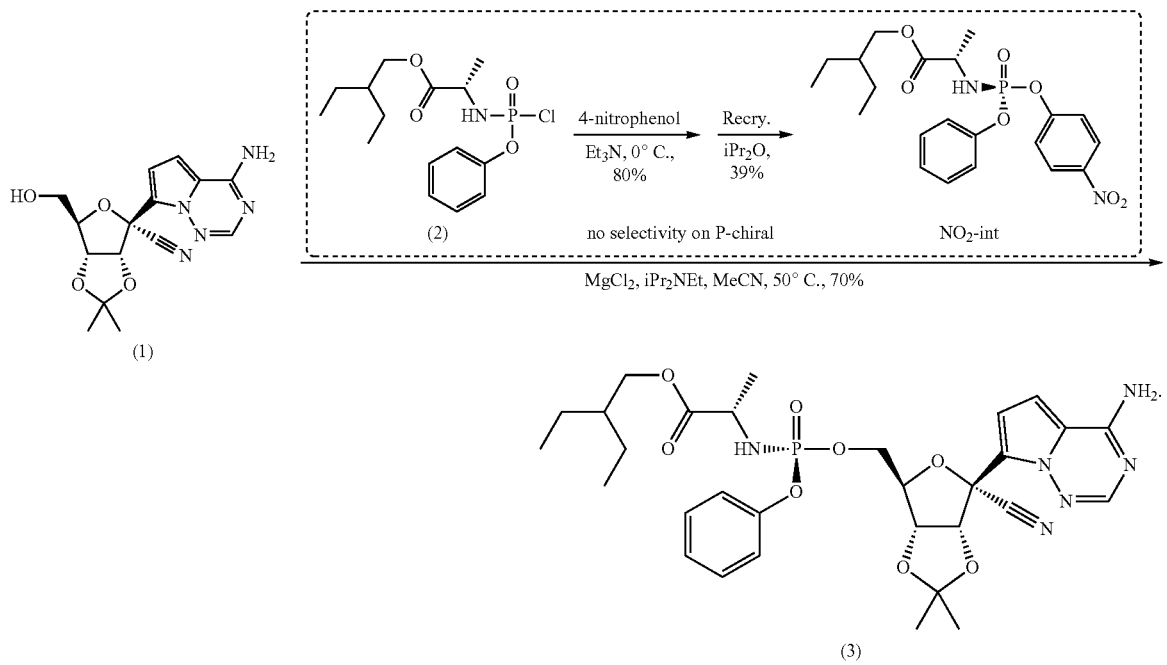

Specifically, the phosphoryl chloride (2) is reacted with 4-nitrophenol to generate racemic intermediate NO2-Int crude product, which is subjected to recrystallization to give optically pure NO2-Int. Then, the nucleoside (1) is reacted with the NO2-Int, and the resultant reaction product is subjected to chiral inversion to obtain the optically pure nucleoside derivative (3). This method involves chiral resolution, and low synthesis efficiency. A catalyst, which is capable of catalyzing the reaction of the nucleoside and phosphoryl chloride to directly and asymmetrically synthesize the P-stereogenic nucleoside derivative (3) and enable the stereoselective construction of the P-stereogenic center, will significantly improve the product yield, simplify the synthesis process, and reduce the reagent consumption. However, the direct catalytic asymmetric synthesis of the P-stereogenic nucleoside derivative (3) has not been reported so far.

SUMMARY

An objective of this application is to provide a method for catalytic asymmetric synthesis of a phosphorus-stereogenic (P-stereogenic) nucleoside derivative and a catalyst used therein. In the synthesis method, the P-stereogenic center is stereoselectively constructed under the catalysis of a chiral bicyclic imidazole catalyst in the presence of a base, so as to enable the asymmetric synthesis of the P-stereogenic nucleoside derivative (3). This application first puts forward a catalysis asymmetric strategy for efficiently preparing the P-stereogenic nucleoside derivative (3), which has advantages of simple operation, high yield and excellent stereoselectivity.

Technical solutions of this application are described as follows.

In a first aspect, this application provides a method for preparing a phosphorus-stereogenic (P-stereogenic) nucleoside derivative, comprising:

subjecting a nucleoside and phosphoryl chloride to asymmetric reaction in a solvent under the catalysis of chiral bicyclic imidazole catalyst in the presence of a base to obtain the P-stereogenic nucleoside derivative of formula (3):

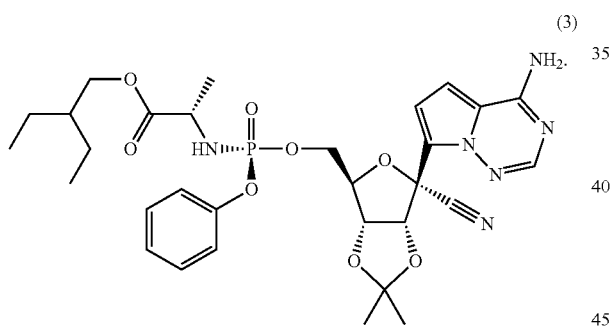

(3)

The P-stereogenic nucleoside derivative (3) can be hydrolyzed to obtain remdesivir.

In an embodiment, the method for synthesizing the P-stereogenic nucleoside derivative through reaction of a nucleoside and phosphoryl chloride under the catalysis of a chiral bicyclic imidazole catalyst is performed through the following scheme:

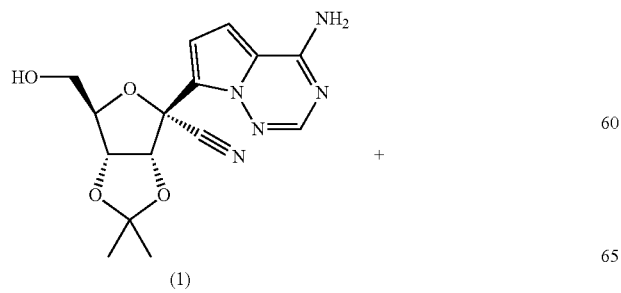

(1)

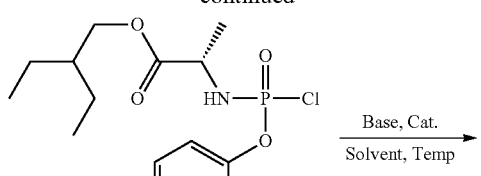

(2)

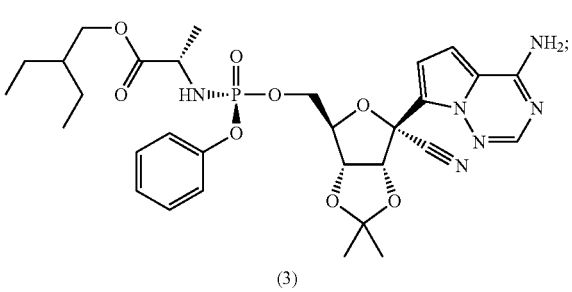

(3)

wherein (1) represents a nucleoside; (2) represents phosphoryl chloride; and (3) represents a P-stereogenic nucleoside derivative.

In an embodiment, the P-stereogenic nucleoside derivative (3) has a maximum productivity of 76%, and a maximum diastereomeric ratio (dr) of 17.5:1.

In an embodiment, the chiral bicyclic imidazole catalyst is a chiral bicyclic imidazole having different substituents.

In an embodiment, the chiral bicyclic imidazole catalyst is selected from the group consisting of:

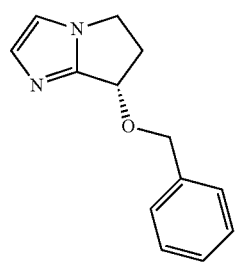

C1

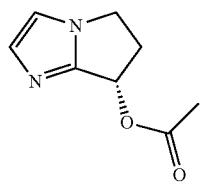

C2

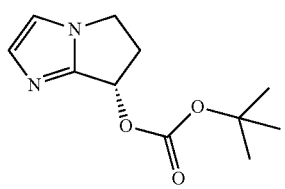

C3

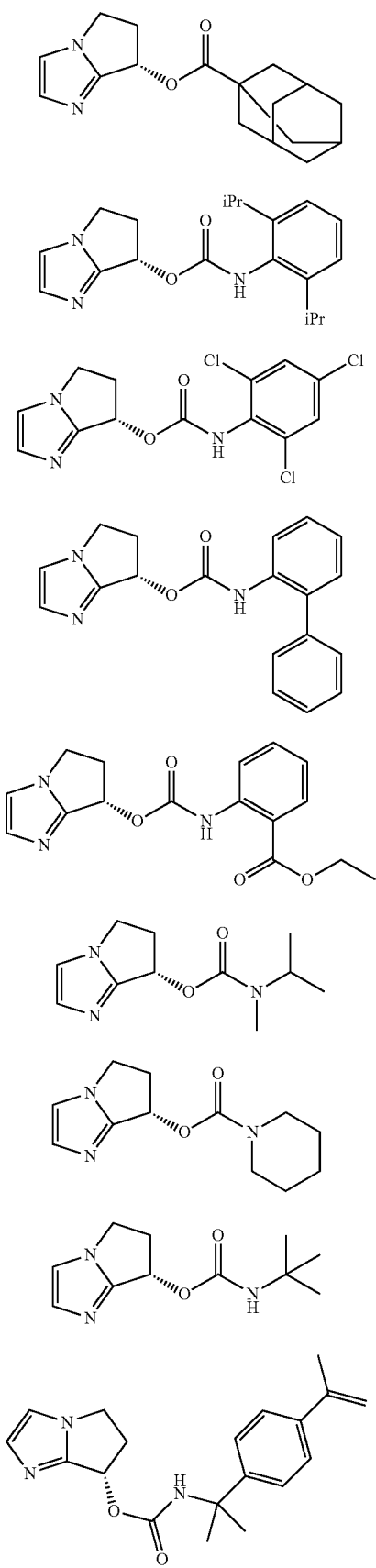

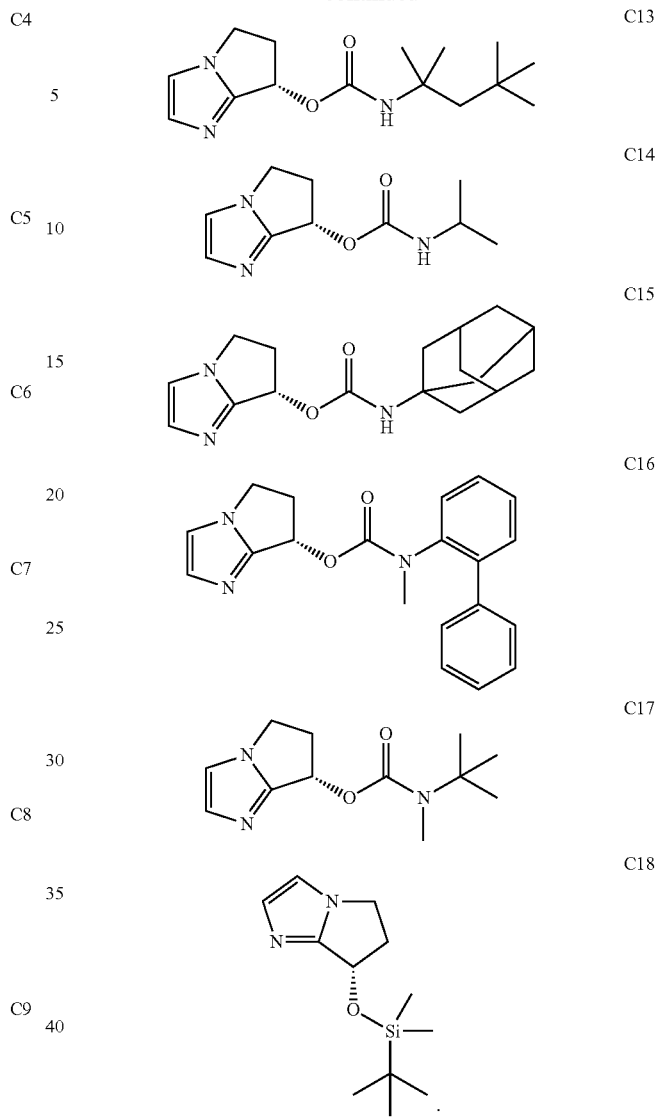

In an embodiment, C1 to C18 are all in S configuration.

In an embodiment, the chiral bicyclic imidazole catalyst is selected from the group consisting of the C5 to C10 and the C12 to C16, preferably the C6, C7, C10, C14, C15 or C16.

In an embodiment, the base is an organic base or an inorganic base.

In an embodiment, the organic base is selected from the group consisting of a $C_1$-$C_{10}$ aliphatic primary amine, a $C_1$-$C_{10}$ aromatic primary amine, a $C_1$-$C_{10}$ aliphatic secondary amine, a $C_1$-$C_{10}$ aromatic secondary amine, a $C_1$-$C_{10}$ aliphatic tertiary amine, a $C_1$-$C_{10}$ aromatic tertiary amine, imidazole, pyridine and a derivative thereof.

In an embodiment, the organic base is selected from the group consisting of triethylamine, NN-diisopropylethylamine, ethylenediamine, tetramethylethylenediamine, trimethylethylenediamine, N,N'-dimethylethylenediamine, N,N-dimethylethylenediamine and 2,6-lutidine.

In an embodiment, the inorganic base is selected from the group consisting of sodium carbonate, potassium carbonate, cesium carbonate, disodium hydrogen phosphate, sodium bicarbonate and potassium bicarbonate.

In an embodiment, the solvent is selected from the group consisting of methylbenzene, diethyl ether, 1,3-dioxolane, 1,4-dioxane, tetrahydrofuran, dichloromethane, trichloromethane, 1,2-dichloroethane, ethyl acetate, acetone, acetonitrile and a combination thereof.

In an embodiment, a molar ratio of the chiral bicyclic imidazole catalyst to the nucleoside is 1:(5~100), preferably 1:(5~10).

In an embodiment, the step of "subjecting a nucleoside and phosphoryl chloride to asymmetric reaction in a solvent under the catalysis of a chiral bicyclic imidazole catalyst in the presence of a base" specifically comprises subjecting a nucleoside and phosphoryl chloride in a solvent under a synergistic effect of the catalysis of the chiral bicyclic imidazole catalyst and the base at the same time, such that the product can have a higher productivity maximumly reaching 76%, and a better diastereomeric ratio (dr) maximumly reaching 17.5:1.

In an embodiment, a molar ratio of the nucleoside to the phosphoryl chloride is 1: (0.5~3.0), preferably 1: (1.2~2.0)

In an embodiment, a molar ratio of the nucleoside to the base is 1:(1.0~4.0), preferably 1:(1.5~3.0).

In an embodiment, the nucleoside is prepared into a solution with a concentration of 0.02~1 M, preferably 0.1~0.5 M, with the solvent to participate in the asymmetric catalytic reaction.

In an embodiment, the asymmetric reaction is performed at −100~80° C. for 1-72 h, preferably at −80~25° C. for 6-24 h.

In a second aspect, this application provides a chiral bicyclic imidazole catalyst, wherein the chiral bicyclic imidazole catalyst is selected from the group consisting of:

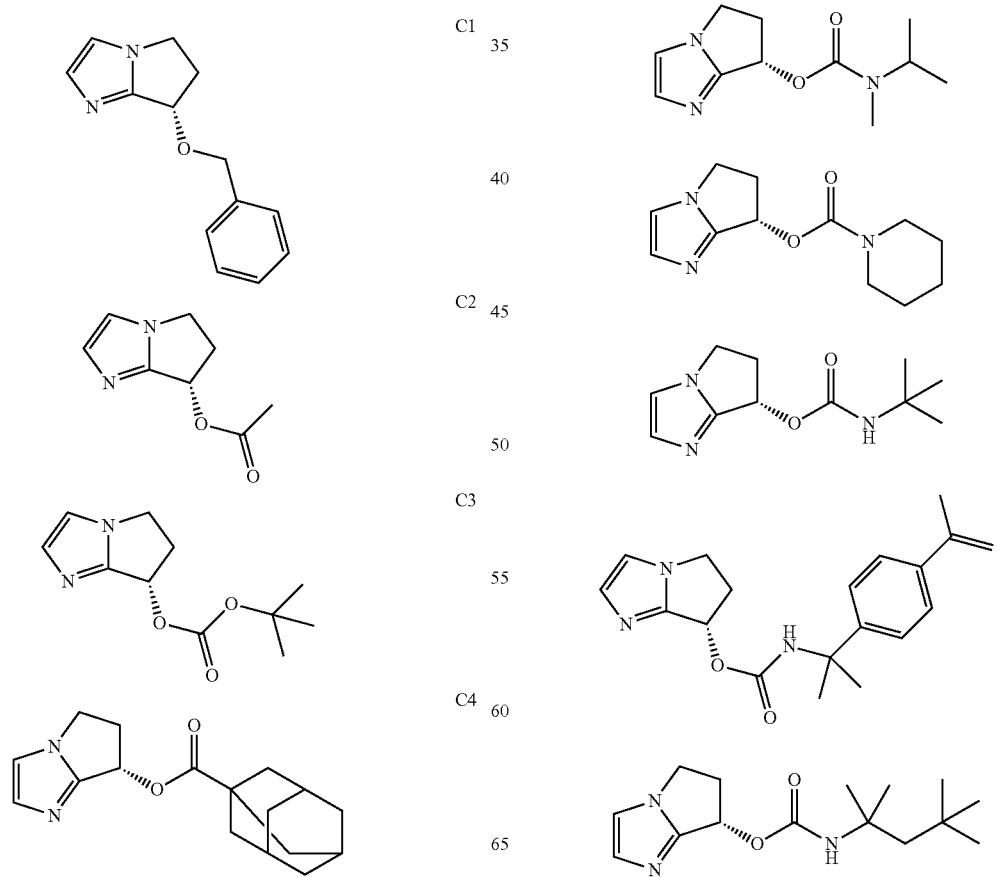

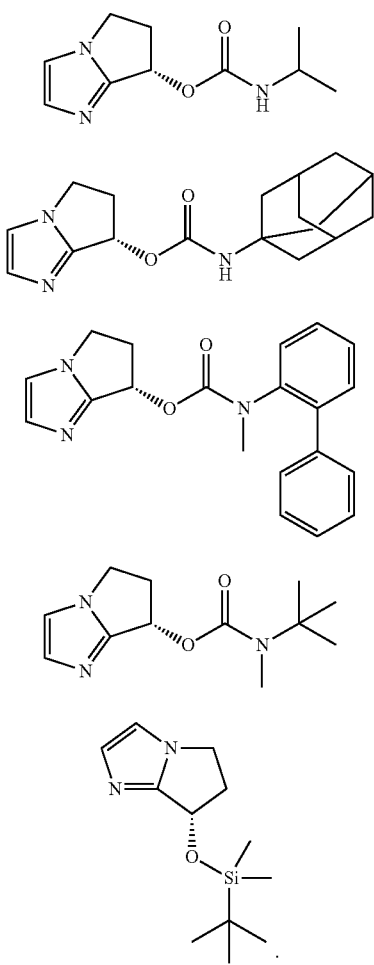

In an embodiment, the chiral bicyclic imidazole catalyst is configured to catalyze the asymmetric reaction between the nucleoside and phosphoryl chloride to synthesize the P-stereogenic nucleoside derivative.

Compared with the prior art, this application has the following beneficial effects.

(1) The chiral imidazole catalyst designed and synthesized in this application has simple synthesis and low cost.

(2) The asymmetric synthesis of the P-stereogenic nucleoside derivative under the catalysis of the chiral imidazole catalyst can directly obtain the chiral nucleoside derivative with a preferred configuration, which greatly enhances the synthesis efficiency, and increases the yield from 22% (reported in the literatures) to 73% (with phosphoryl chloride as raw material). Moreover, the diastereomeric ratio (dr) of the product can reach 17.5:1.

(3) The synthesis method provide herein has readily-available raw materials, mild reaction conditions, simple operation, low cost, easy separation and purification, high yield, and excellent chemical purity and optical purity, and thus is suitable for the industrial production.

DETAILED DESCRIPTION OF EMBODIMENTS

In order to clearly explain the technical solutions, this application will be described in detail below with reference to the embodiments. It should be understood by those skilled in the art that the embodiments are merely illustrative, and are not intended to limit the scope of the disclosure. It should be noted that any improvements and modifications made by those skilled in the art without departing from the spirit of this application shall fall within the scope of this application defined by the appended claims.

Example 1 Preparation of Phosphorus-Stereogenic (P-Stereogenic) Nucleoside Derivative (3)

Nucleoside (1) (66.3 mg, 0.2 mmol, 1.0 eq), a bicyclic imidazole catalyst C15 (12.1 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (2 mL) and 2,6-lutidine (35.0 µL, 0.3 mmol, 1.5 eq) were added in sequence. The reaction mixture was added dropwise with phosphoryl chloride (2) (104.3 mg, 0.3 mmol, 1.5 eq) at −20° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 14.6:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (86.5 mg and 67% yield).

$^1$H-NMR (400 MHz, methanol—d$_4$) δ7.86 (s, 1H), 7.30-7.23 (m, 2H), 7.18-7.11 (m, 3H), 6.91 (d, J=4.6 Hz, 1H), 6.89 (d, J=4.6 Hz, 1H), 5.34 (d, J=6.7 Hz, 1H), 4.99 (dd, J=6.7, 3.5 Hz, 1H), 4.59-4.53 (m, 1H), 4.35-4.24 (m, 2H), 4.02 (dd, J=10.9, 5.8 Hz, 1H), 3.91 (dd, J=10.9, 5.7 Hz, 1H), 3.88-3.79 (m, 1H), 1.70 (s, 3H), 1.51-1.42 (m, 1H), 1.40 (s, 3H), 1.36-1.23 (m, 7H), 0.86 (t, J=7.5 Hz, 6H);

$^{13}$C-NMR (100 MHz, methanol-d$_4$) δ 174.9, 174.9, 157.1, 152.1, 152.0, 148.3, 130.7, 126.1, 126.1, 124.6, 121.4, 121.3, 118.3, 117.8, 117.0, 112.4, 102.5, 85.7, 84.9, 84.8, 83.1, 82.6, 68.1, 67.0, 67.0, 51.5, 41.7, 26.5, 25.5, 24.2, 24.2, 20.5, 20.4, 11.3, 11.3; and $^{31}$P-NMR (162 MHz, methanol-d$_4$) δ3.38 (s).

Example 2 Preparation of P-Stereogenic Nucleoside Derivative (3)

Nucleoside (1) (66.3 mg, 0.2 mmol, 1.0 eq), a bicyclic imidazole catalyst C1 (8.6 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (6 mL) and triethylamine (55.6 µL, 0.4 mmol, 2.0 eq) were added in sequence to the reaction system. The reaction mixture was added dropwise with phosphoryl chloride (2) (104.3 mg, 0.3 mmol, 1.5 eq) at −40° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 2.9:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (20.5 mg and 16% yield).

Example 3 Preparation of P-Stereogenic Nucleoside Derivative (3)

Nucleoside (1) (66.3 mg, 0.2 mmol, 1.0 eq), a bicyclic imidazole catalyst C2 (6.7 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (6 mL) and 2,6-lutidine (70.0 µL, 0.6 mmol, 3.0 eq) were added in sequence to the reaction system. The reaction mixture was added dropwise with phosphoryl chloride (2) (104.3 mg, 0.3 mmol, 1.5 eq) at −40° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 1.8:1. The crude product was purified by silica-gel column chromatography (particle size: 100~200 mesh; specific surface area: 300-400 $m^2/g$; and mobile phase: petroleum ether and ethyl acetate in a volume ratio of 1:10) to obtain the P-stereogenic nucleoside derivative (3) (23.2 mg and 18% yield).

Example 4 Preparation of P-Stereogenic Nucleoside Derivative (3)

Nucleoside (1) (66.3 mg, 0.2 mmol, 1.0 eq), a bicyclic imidazole catalyst C3 (9.0 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (6 mL) and potassium carbonate (46.6 µL, 0.4 mmol, 2.0 eq) and 2,6-lutidine (46.6 µL, 0.4 mmol, 2.0 eq) were added in sequence to the reaction system. The reaction mixture was added dropwise with phosphoryl chloride (2) (104.3 mg, 0.3 mmol, 1.5 eq) at −40° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 1.5:1. The crude product was purified by silica-gel column chromatography (particle size: 100~200 mesh; specific surface area: 300-400 $m^2/g$; and mobile phase: petroleum ether and ethyl acetate in a volume ratio of 1:10) to obtain the P-stereogenic nucleoside derivative (3) (27.1 mg and 21% yield).

Example 5 Preparation of P-Stereogenic Nucleoside Derivative (3)

Nucleoside (1) (66.3 mg, 0.2 mmol, 1.0 eq), a bicyclic imidazole catalyst C4 (11.5 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (6 mL) and N,N'-dimethylethylenediamine (43.7 µL, 0.4 mmol, 2.0 eq) were added in sequence to the reaction system. The reaction mixture was added dropwise with phosphoryl chloride (2) (104.3 mg, 0.3 mmol, 1.5 eq) at −40° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 2.1:1. The crude product was purified by silica-gel column chromatography (particle size: 100~200 mesh; specific surface area: 300-400 $m^2/g$; and mobile phase: petroleum ether and ethyl acetate in a volume ratio of 1:10) to obtain the P-stereogenic nucleoside derivative (3) (19.3 mg and 15% yield).

Example 6 Preparation of P-Stereogenic Nucleoside Derivative (3)

Nucleoside (1) (66.3 mg, 0.2 mmol, 1.0 eq), a bicyclic imidazole catalyst C5 (13.1 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (2 mL) and 2,6-lutidine (46.6 µL, 0.4 mmol, 2.0 eq) were added in sequence to the reaction system. The reaction mixture was added dropwise with phosphoryl chloride (2) (104.3 mg, 0.3 mmol, 1.5 eq) at −40° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 2.9:1. The crude product was purified by silica-gel column chromatography (particle size: 100~200 mesh; specific surface area: 300-400 $m^2/g$; and mobile phase: petroleum ether and ethyl acetate in a volume ratio of 1:10) to obtain the P-stereogenic nucleoside derivative (3) (29.6 mg and 23% yield).

Example 7 Preparation of P-Stereogenic Nucleoside Derivative (3)

Nucleoside (1) (66.3 mg, 0.2 mmol, 1.0 eq), a bicyclic imidazole catalyst C6 (13.9 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (2 mL) and 2,6-lutidine (93.2 µL, 0.8 mmol, 4.0 eq) were added in sequence to the reaction system. The reaction mixture was added dropwise with phosphoryl chloride (2) (208.6 mg, 0.6 mmol, 3.0 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 4.4:1. The crude product was purified by silica-gel column chromatography (particle size: 100~200 mesh; specific surface area: 300-400 $m^2/g$; and mobile phase: petroleum ether and ethyl acetate in a volume ratio of 1:10) to obtain the P-stereogenic nucleoside derivative (3) (69.4 mg and 54% yield).

Example 8 Preparation of P-Stereogenic Nucleoside Derivative (3)

Nucleoside (1) (66.3 mg, 0.2 mmol, 1.0 eq), a bicyclic imidazole catalyst C7 (12.8 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (2 mL) and 2,6-lutidine (46.6 µL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 3.7:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (65.6 mg and 51% yield).

Example 9 Preparation of P-Stereogenic Nucleoside Derivative (3)

Nucleoside (1) (66.3 mg, 0.2 mmol, 1.0 eq), a bicyclic imidazole catalyst C8 (12.6 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (1 mL) and 2,6-lutidine (46.6 μL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 3.2:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (46.3 mg and 36% yield).

Example 10 Preparation of P-Stereogenic Nucleoside Derivative (3)

Nucleoside (1) (66.3 mg, 0.2 mmol, 1.0 eq), a bicyclic imidazole catalyst C9 (10.1 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (4 mL) and 2,6-lutidine (46.6 μL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 7.0:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (28.3 mg and 22% yield).

Example 11 Preparation of P-Stereogenic Nucleoside Derivative (3)

Nucleoside (1) (66.3 mg, 0.2 mmol, 1.0 eq), a bicyclic imidazole catalyst C10 (9.4 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (2 mL) and 2,6-lutidine (46.6 μL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 5.2:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (70.8 mg and 55% yield).

Example 12 Preparation of P-Stereogenic Nucleoside Derivative (3)

Nucleoside (1) (66.3 mg, 0.2 mmol, 1.0 eq), a bicyclic imidazole catalyst C11 (8.9 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (6 mL) and N,N-diisopropylethylamine (66.1 μL, 0.4 mmol, 2.0 eq) were added in sequence to the reaction system. The reaction mixture was added dropwise with phosphoryl chloride (2) (104.3 mg, 0.3 mmol, 1.5 eq) at −40° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 5.5:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (15.3 mg and 12% yield).

Example 13 Preparation of P-Stereogenic Nucleoside Derivative (3)

Nucleoside (1) (66.3 mg, 0.2 mmol, 1.0 eq), a bicyclic imidazole catalyst C12 (13.0 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (6 mL) and 2,6-lutidine (46.6 μL, 0.4 mmol, 2.0 eq) were added in sequence to the reaction system. The reaction mixture was added dropwise with phosphoryl chloride (2) (104.3 mg, 0.3 mmol, 1.5 eq) at −40° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 5.9:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (57.7 mg and 45% yield).

Example 14 Preparation of P-Stereogenic Nucleoside Derivative (3)

Nucleoside (1) (66.3 mg, 0.2 mmol, 1.0 eq), a bicyclic imidazole catalyst C13 (11.2 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (6 mL) and 2,6-lutidine (46.6 μL, 0.4 mmol, 2.0 eq) were added in sequence to the reaction system. The reaction mixture was added dropwise with phosphoryl chloride (2) (104.3 mg, 0.3 mmol, 1.5 eq) at −30° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 9.3:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (42.9 mg and 33% yield).

Example 15 Preparation of P-Stereogenic Nucleoside Derivative (3)

Nucleoside (1) (66.3 mg, 0.2 mmol, 1.0 eq), a bicyclic imidazole catalyst C14 (8.4 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (6 mL) and 2,6-lutidine (46.6 μL, 0.4 mmol, 2.0 eq) were added in sequence to the reaction system. The reaction mixture was added dropwise with phosphoryl chloride (2) (104.3 mg, 0.3 mmol, 1.5 eq) at −30° C., reacted under stirring for 36 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 9.7:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (49.8 mg and 39% yield).

Example 16 Preparation of P-Stereogenic Nucleoside Derivative (3)

Nucleoside (1) (66.3 mg, 0.2 mmol, 1.0 eq), a bicyclic imidazole catalyst C16 (13.3 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (2 mL) and 2,6-lutidine (46.6 μL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 36 h, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 2.5:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (74.8 mg and 58% yield).

Example 17 Preparation of P-Stereogenic Nucleoside Derivative (3)

Nucleoside (1) (66.3 mg, 0.2 mmol, 1.0 eq), a bicyclic imidazole catalyst C17 (13.3 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (4 mL) and N,N-diisopropylethylamine (66.1 μL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 2.6:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (30.7 mg and 24% yield).

Example 18 Preparation of P-Stereogenic Nucleoside Derivative (3)

Nucleoside (1) (66.3 mg, 0.2 mmol, 1.0 eq), a bicyclic imidazole catalyst C18 (9.5 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (4 mL) and triethylamine (55.6 μL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 3.8:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (24.7 mg and 19% yield).

Example 19 Preparation of P-Stereogenic Nucleoside Derivative (3)

Nucleoside (1) (66.3 mg, 0.2 mmol, 1.0 eq), a bicyclic imidazole catalyst C11 (55.6 μL, 0.4 mmol, 2.0 eq) and a 4 Å molecular sieve (80.0 mg) were added to a dry 10 mL reaction tube, and then the reaction tube was vacuumed and replaced with nitrogen gas 3 times. After that, dichloromethane (6 mL) and 2,6-lutidine (46.6 μL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 16 h, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 2.8:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (25.7 mg and 20% yield).

Example 20 Preparation of P-Stereogenic Nucleoside Derivative (3)

Nucleoside (1) (66.3 mg, 0.2 mmol, 1.0 eq), a bicyclic imidazole catalyst C11 (17.86 mg, 0.08 mmol, 0.4 eq) and a 4 Å molecular sieve (80.0 mg) were added to a dry 10 mL reaction tube, and then the reaction tube was vacuumed and replaced with nitrogen gas 3 times. After that, methylbenzene (6 mL) and N,N-diisopropylethylamine (66.1 μL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 16 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 2.5:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (29.6 mg and 23% yield).

Example 21 Preparation of P-Stereogenic Nucleoside Derivative (3)

Nucleoside (1) (66.3 mg, 0.2 mmol, 1.0 eq), a bicyclic imidazole catalyst C11 (8.93 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, 1,3-dioxolane (6 mL) and 2,6-lutidine (46.6 μL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 2.5:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (21.8 mg and 17% yield).

Example 22 Preparation of P-Stereogenic Nucleoside Derivative (3)

Nucleoside (1) (66.3 mg, 0.2 mmol, 1.0 eq), a bicyclic imidazole catalyst C11 (8.93 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, ethyl acetate (6 mL) and 2,6-lutidine (46.6 μL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 16 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 1.9:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (16.7 mg and 13% yield).

Example 23 Preparation of P-Stereogenic Nucleoside Derivative (3)

Nucleoside (1) (66.3 mg, 0.2 mmol, 1.0 eq), a bicyclic imidazole catalyst C11 (8.93 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, acetone (6 mL) and 2,6-lutidine (46.6 μL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 16 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 1.4:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (15.4 mg and 12% yield).

Example 24 Preparation of P-Stereogenic Nucleoside Derivative (3)

Nucleoside (1) (66.3 mg, 0.2 mmol, 1.0 eq), a bicyclic imidazole catalyst C11 (8.93 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, tetrahydrofuran (6 mL) and 2,6-lutidine (46.6 μL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 1.4:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (11.5 mg and 9% yield).

Example 25 Preparation of P-Stereogenic Nucleoside Derivative (3)

Nucleoside (1) (66.3 mg, 0.2 mmol, 1.0 eq), a bicyclic imidazole catalyst C15 (12.1 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (2 mL) and 2,6-lutidine (46.6 μL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 11.8:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (92.3 mg and 72% yield).

Example 26 Preparation of P-Stereogenic Nucleoside Derivative (3)

Nucleoside (1) (66.3 mg, 0.2 mmol, 1.0 eq), a bicyclic imidazole catalyst C15 (12.1 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (2 mL) was added in sequence to the reaction system. The reaction mixture was added dropwise with phosphoryl chloride (2) (104.3 mg, 0.3 mmol, 1.5 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 9.8:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (6.4 mg and 5% yield).

Example 27 Preparation of P-Stereogenic Nucleoside Derivative (3)

Nucleoside (1) (66.3 mg, 0.2 mmol, 1.0 eq), a bicyclic imidazole catalyst C15 (12.1 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (2 mL) and triethylamine (55.6 µL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 4.1:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (48.7 mg and 38% yield).

Example 28 Preparation of P-Stereogenic Nucleoside Derivative (3)

Nucleoside (1) (66.3 mg, 0.2 mmol, 1.0 eq), a bicyclic imidazole catalyst C15 (12.1 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (2 mL) and N,N-diisopropylethylamine (66.1 µL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 8.6:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (39.7 mg and 31% yield).

Example 29 Preparation of P-Stereogenic Nucleoside Derivative (3)

Nucleoside (1) (66.3 mg, 0.2 mmol, 1.0 eq), a bicyclic imidazole catalyst C15 (12.1 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (2 mL) and 1,8-diazabicyclo[5.4.0]undec-7-ene (59.8 µL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 1.7:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (29.5 mg and 23% yield).

Example 30 Preparation of P-Stereogenic Nucleoside Derivative (3)

Nucleoside (1) (66.3 mg, 0.2 mmol, 1.0 eq), a bicyclic imidazole catalyst C15 (12.1 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (2 mL) and 2,6-lutidine (46.6 µL, 0.4 mmol, 2.0 eq) were added in sequence to the reaction system. The reaction mixture was added dropwise with phosphoryl chloride (2) (104.3 mg, 0.3 mmol, 1.5 eq) at −30° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 17.5:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (92.0 mg and 71% yield).

Example 31 Preparation of P-Stereogenic Nucleoside Derivative (3)

Nucleoside (1) (66.3 mg, 0.2 mmol, 1.0 eq), a bicyclic imidazole catalyst C11 (8.93 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (2 mL) and triethylamine (55.6 µL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 2.5:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (20.4 mg and 16% yield).

Example 32 Preparation of P-Stereogenic Nucleoside Derivative (3)

Nucleoside (1) (66.3 mg, 0.2 mmol, 1.0 eq), a bicyclic imidazole catalyst C11 (8.93 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (6 mL) and N,N-diisopropylethylamine (66.1 µL, 0.4 mmol, 2.0 eq) were added in sequence to the reaction system. The reaction mixture was added dropwise with phosphoryl chloride (2) (139.1 mg, 0.4 mmol, 2.0 eq) at −30° C., reacted under stirring for 12 h, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 3.8:1. The crude product was purified by silica-gel column chromatography (particle size: 100~200 mesh; specific surface area: 300-400 m$^2$/g; and mobile phase: petroleum ether and ethyl acetate in a volume ratio of 1:10) to obtain the P-stereogenic nucleoside derivative (3) (21.8 mg and 17% yield).

Example 33 Preparation of P-Stereogenic Nucleoside Derivative (3)

Nucleoside (1) (99.4 mg, 0.2 mmol, 1.5 eq), a bicyclic imidazole catalyst C15 (12.1 mg, 0.04 mmol, 0.2 eq) and a 4 Å molecular sieve (80.0 mg) were added to a dry 10 mL reaction tube, and then the reaction tube was vacuumed and replaced with nitrogen gas 3 times. After that, dichloromethane (2 mL) and 2,6-lutidine (46.6 µL, 0.4 mmol, 2.0 eq) were added in sequence to the reaction system. The reaction mixture was added dropwise with phosphoryl chloride (2) (69.6 mg, 0.4 mmol, 1.0 eq) at −10° C., reacted under stirring for 12 hours, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 8.8:1. The crude product was purified by silica-gel column chromatography (mobile phase: petroleum ether and ethyl acetate in a volume ratio of 1:10) to obtain the P-stereogenic nucleoside derivative (3) (93.5 mg and 73% yield).

Example 34 Preparation of P-Stereogenic Nucleoside Derivative (3)

Nucleoside (1) (66.3 mg, 0.2 mmol, 1.0 eq), a bicyclic imidazole catalyst C15 (24.2 mg, 0.08 mmol, 0.4 eq) and a 4 Å molecular sieve (80.0 mg) were added to a dry 10 mL reaction tube, and then the reaction tube was vacuumed and replaced with nitrogen gas 3 times. After that, dichloromethane (2 mL) and 2,6-lutidine (46.6 µL, 0.4 mmol, 2.0 eq) were added in sequence to the reaction system. The reaction mixture was added dropwise with phosphoryl chloride (2) (104.3 mg, 0.3 mmol, 1.5 eq) at −10° C., reacted under stirring for 12 h, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 11.5:1. The crude product was purified by silica-gel column chromatography (mobile phase: petroleum ether and ethyl acetate in a volume ratio of 1:10) to obtain the P-stereogenic nucleoside derivative (3) (97.8 mg and 76% yield).

Example 35 Preparation of P-Stereogenic Nucleoside Derivative (3)

A bicyclic imidazole catalyst C15 (6.1 mg, 0.02 mmol, 0.1 eq) and a 4 Å molecular sieve (80.0 mg) were added to a dry 10 mL reaction tube, and then the reaction tube was vacuumed and replaced with nitrogen gas 3 times. After that, dichloromethane (3 mL), 2,6-lutidine (46.6 µL, 0.4 mmol, 2.0 eq) and phosphoryl chloride 2 (104.3 mg, 0.3 mmol, 1.5 eq) were added in sequence to the reaction tube. At −30° C., the reaction mixture was added dropwise with a solution of nucleoside (1) (66.3 mg, 0.2 mmol, 1.0 eq) and 1 mL of dichloromethane via an injection pump under a speed of 0.1 mL/min, reacted under stirring for 12 h, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 12.4:1. The crude product was purified by silica-gel column chromatography (mobile phase: petroleum ether and ethyl acetate in a volume ratio of 1:10) to obtain the P-stereogenic nucleoside derivative (3) (84.1 mg and 65% yield).

Example 36 Preparation of P-Stereogenic Nucleoside Derivative (3)

A bicyclic imidazole catalyst C15 (6.1 mg, 0.02 mmol, 0.1 eq) and a 4 Å molecular sieve (80.0 mg) were added to a dry 10 mL reaction tube, and then the reaction tube was vacuumed and replaced with nitrogen gas 3 times. After that, dichloromethane (3 mL), 2,6-lutidine (46.6 µL, 0.4 mmol, 2.0 eq) and phosphoryl chloride 2 (104.3 mg, 0.3 mmol, 1.5 eq) were added in sequence to the reaction tube. At −30° C., the reaction mixture was added dropwise with a solution of nucleoside (1) (66.3 mg, 0.2 mmol, 1.0 eq) and 1 mL of dichloromethane via an injection pump under a speed of 0.2 mL/min, reacted under stirring for 12 h, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 11.5:1. The crude product was purified by silica-gel column chromatography (mobile phase: petroleum ether and ethyl acetate in a volume ratio of 1:10) to obtain the P-stereogenic nucleoside derivative (3) (87.7 mg and 68% yield).

Example 37 Preparation of P-Stereogenic Nucleoside Derivative (3)

A bicyclic imidazole catalyst C15 (6.1 mg, 0.02 mmol, 0.1 eq) and a 4 Å molecular sieve (80.0 mg) were added to a dry 10 mL reaction tube, and then the reaction tube was vacuumed and replaced with nitrogen gas 3 times. After that, dichloromethane (3 mL), 2,6-lutidine (46.6 µL, 0.4 mmol, 2.0 eq) and phosphoryl chloride 2 (104.3 mg, 0.3 mmol, 1.5 eq) were added in sequence. At −30° C., the reaction mixture was added with a solution of nucleoside (1) (66.3 mg, 0.2 mmol, 1.0 eq) and 1 mL of dichloromethane via an injection pump quickly, and reacted under stirring for 12 h, quenched with 0.5 mL of methanol for 30 min, and restored to room temperature. The reaction mixture was subjected to rotary evaporation, and analyzed by nuclear magnetic resonance (NMR), where the diastereomeric ratio (dr) was measured to be 9.1:1. The crude product was purified by silica-gel column chromatography (mobile phase: petroleum ether and ethyl acetate in a volume ratio of 1:10) to obtain the P-stereogenic nucleoside derivative (3) (88.6 mg and 69% yield).

Example 38 Preparation of Chiral Bicyclic Imidazole Catalyst C1

To a dry reaction flask were added (S)-6,7-dihydro-5H-pyrrolo[1,2-A]imidazol-7-ol (300 mg, 2.4 mmol, 1.0 eq) and 30 mL of tetrahydrofuran. The reaction flask was batchwise added with sodium hydride (60 wt. %, 116 mg, 2.9 mmol, 1.2 eq) at 0° C. and stirred for 30 min. Then, the reaction mixture was added with benzyl bromide (0.43 mL, 3.6 mmol, 1.5 eq) and reacted at 20° C. for 12 h. After that, the reaction mixture was quenched with 30 mL of water, and subjected to extraction with 30 mL of dichloromethane. The organic phases were combined, dried with magnesium sulfate anhydrous and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C1 (378 mg and 73% yield).

$^1$HNMR (400 MHz, CDCl$_3$) δ7.41-7.27 (m, 5H), 7.16 (d, J=1.2 Hz, 1H), 6.93 (d, J=1.2 Hz, 1H), 4.90 (d, J=11.6 Hz, 1H), 4.83 (dd, J=7.2 Hz, 2.0 Hz, 1H), 4.73 (d, J=11.6 Hz, 1H), 4.21-4.13 (m, 1H), 3.96-3.89 (m, 1H), 2.92-2.82 (m, 1H), 2.67-2.59 (m, 1H); and $^{13}$CNMR (100 MHz, CDCl$_3$) δ153.5, 137.9, 133.8, 128.4, 128.1, 127.7, 115.0, 71.1, 70.8, 43.1, 35.3.

Example 39 Preparation of Chiral Bicyclic Imidazole Catalyst C2

To a dry reaction flask were added (S)-6,7-dihydro-5H-pyrrolo[1,2-A]imidazol-7-ol (300 mg, 2.4 mmol, 1.0 eq) and 20 mL of dichloromethane and triethylamine (1.08 mL, 7.2 mmol, 3.0 eq) followed by stirring for 5 min. The reaction flask was added with acetic anhydride (0.34 mL, 3.6 mmol, 1.5 eq) at 20° C. and reacted for 12 h. After that, the reaction mixture was quenched with 30 mL of water, and subjected to extraction with 30 mL of dichloromethane. The organic phases were combined, dried with magnesium sulfate anhydrous, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C2 (305 mg and 76% yield).

$^1$HNMR (400 MHz, CDCl$_3$) δ 7.19 (s, 1H), 6.97 (s, 1H), 5.99 (dd, J=7.2 Hz, 2.4 Hz, 1H), 4.22-4.11 (m, 1H), 4.05-3.95 (m, 1H), 3.14-3.01 (m, 1H), 2.61-2.49 (m, 1H), 2.11 (s, 3H); and $^{13}$CNMR (100 MHz, CDCl$_3$) δ169.8, 150.5, 134.0, 115.2, 66.6, 42.4, 34.3, 20.5.

Example 40 Preparation of Chiral Bicyclic Imidazole Catalyst C3

To a dry reaction flask were added (S)-6,7-dihydro-5H-pyrrolo[1,2-A]imidazol-7-ol (300 mg, 2.4 mmol, 1.0 eq) and 30 mL of tetrahydrofuran. The reaction flask was batchwise added with sodium hydride (60 wt. %, 116 mg, 2.9 mmol, 1.2 eq) at 0° C., and stirred for 30 min. Then, the reaction mixture was added with di-t-butyl dicarbonate (0.83 mL, 3.6 mmol, 1.5 eq) and reacted at 20° C. for 12 h. After that, the reaction mixture was quenched with 30 mL of water, and subjected to extraction with 30 mL of dichloromethane. The organic phases were combined, dried with magnesium sulfate anhydrous and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C3 (385.0 mg and 71% yield).

$^1$HNMR (500 MHz, CDCl$_3$) δ7.18 (d, J=1.2 Hz, 1H), 6.93 (d, J=1.3 Hz, 1H), 5.89 (dd, J=6.8, 1.9 Hz, 1H), 4.22-4.14 (m, 1H), 4.03-3.95 (m, 1H), 3.08-2.99 (m, 1H), 2.69-2.61 (m, 1H), 1.50 (s, 9H); and $^{13}$CNMR (126 MHz, CDCl$_3$) δ152.7, 150.8, 134.9, 115.4, 82.9, 69.3, 42.9, 34.9, 27.8.

Example 41 Preparation of Chiral Bicyclic Imidazole Catalyst C4

To a dry reaction flask were added (S)-6,7-dihydro-5H-pyrrolo[1,2-A]imidazol-7-ol (300 mg, 2.4 mmol, 1.0 eq) and 20 mL of dichloromethane and triethylamine (1.68 mL, 12.1 mmol, 5.0 eq) followed by stirring for 5 min. The reaction mixture was added with adamantanecarbonyl chloride (497 mg, 2.5 mmol, 1.05 eq), and reacted at 20° C. for 12 h. After that, the reaction mixture was quenched with 30 mL of water, and subjected to extraction with 30 mL of dichloromethane. The organic phases were combined, dried with magnesium sulfate anhydrous, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C4 (392 mg and 57% yield).

$^1$HNMR (500 MHz, CDCl$_3$) δ7.20 (s, 1H), 6.96 (s, 1H), 5.96 (dd, J=7.4, 2.9 Hz, 1H), 4.20-4.10 (m, 1H), 4.03-3.94 (m, 1H), 3.14-3.03 (m, 1H), 2.50-2.40 (m, 1H), 2.03-1.97 (m, 3H), 1.92-1.86 (m, 6H), 1.74-1.64 (m, 6H); and $^{13}$CNMR (126 MHz, CDCl$_3$) δ177.3, 151.4, 134.8, 115.5, 66.9, 43.0, 40.9, 39.0, 38.8, 36.736.5, 35.3, 28.2, 28.0.

Example 42 Preparation of Chiral Bicyclic Imidazole Catalyst C5

To a dry reaction flask were added (S)-6,7-dihydro-5H-pyrrolo[1,2-A]imidazol-7-ol (200 mg, 1.6 mmol, 1.0 eq) and 20 mL of tetrahydrofuran. The reaction flask was batchwise added with sodium hydride (60 wt. %, 77 mg, 1.9 mmol, 1.2 eq) at 0° C., and stirred for 30 min. Then, the reaction mixture was added with 2,6-diisopropylphenyl isocyanate (0.52 mL, 2.4 mmol, 1.5 eq), and reacted at 20° C. for 12 h. After that, the reaction mixture was quenched with 30 mL of water, and subjected to extraction with 30 mL of dichloromethane. The organic phases were combined, dried with magnesium sulfate anhydrous, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C5 (402 mg and 76% yield).

$^1$HNMR (500 MHz, CDCl$_3$) δ7.31-7.27 (m, 1H), 7.21 (s, 1H), 7.17 (s, 1H), 7.16 (s, 1H), 6.98 (s, 1H), 6.46 (s, 1H), 5.94 (dd, J=7.1, 2.8 Hz, 1H), 4.24-4.16 (m, 1H), 4.04-3.96 (m, 1H), 3.22-3.09 (m, 3H), 2.69-2.60 (m, 1H), 1.23 (d, J=6.9 Hz, 6H), 1.19 (d, J=6.9 Hz, 6H); and $^{13}$CNMR (126 MHz, CDCl$_3$) δ154.7, 151.2, 146.8, 134.8, 130.5, 128.4, 123.5, 115.6, 68.4, 43.0, 35.7, 28.6, 23.8, 23.5.

Example 43 Preparation of Chiral Bicyclic Imidazole Catalyst C6

To a dry reaction flask were added (S)-6,7-dihydro-5H-pyrrolo[1,2-A]imidazol-7-ol (200 mg, 1.6 mmol, 1.0 eq) and 20 mL of tetrahydrofuran. The reaction flask was batchwise added with sodium hydride (60 wt. %, 77 mg, 1.9 mmol, 1.2 eq) at 0° C., and stirred for 30 min. Then, the reaction mixture was added with 2,4,6-trichlorophenyl isocyanate (538 mg, 2.4 mmol, 1.5 eq), and reacted at 20° C. for 12 h. After that, the reaction mixture was quenched with 30 mL of water, and subjected to extraction with 30 mL of dichloromethane. The organic phases were combined, dried with magnesium sulfate anhydrous, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C6 (229 mg and 41% yield).

$^1$HNMR (500 MHz, CDCl$_3$) δ8.18 (s, 1H), 7.38 (s, 2H), 7.16 (s, 1H), 6.94 (s, 1H), 5.98 (dd, J=7.3, 2.7 Hz, 1H), 4.22-4.14 (m, 1H), 4.03-3.93 (m, 1H), 3.20-3.07 (m, 1H), 2.74-2.64 (m, 1H); and $^{13}$CNMR (126 MHz, CDCl$_3$) δ153.3, 150.9, 134.9, 134.7, 133.4, 131.2, 128.6, 115.6, 100.1, 68.9, 43.1, 35.5.

Example 44 Preparation of Chiral Bicyclic Imidazole Catalyst C7

To a dry reaction flask were added (S)-6,7-dihydro-5H-pyrrolo[1,2-A]imidazol-7-ol (200 mg, 1.6 mmol, 1.0 eq) and 20 mL of tetrahydrofuran. The reaction flask was batchwise added with sodium hydride (60 wt. %, 77 mg, 1.9 mmol, 1.2 eq) at 0° C., and stirred for 30 min. Then, the reaction mixture was added with 2-biphenylyl isocyanate (472 mg, 2.4 mmol, 1.5 eq), and reacted at 20° C. for 12 h. After that, the reaction mixture was quenched with 30 mL of water, and subjected to extraction with 30 mL of dichloromethane, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C7 (423 mg and 82% yield).

$^1$HNMR (500 MHz, CDCl$_3$) δ8.19 (d, J=8.3 Hz, 1H), 7.48-7.41 (m, 2H), 7.41-7.30 (m, 4H), 7.22-7.10 (m, 3H), 6.94 (s, 1H), 6.75 (s, 1H), 5.98 (dd, J=7.3, 2.6 Hz, 1H), 4.17-4.09 (m, 1H), 4.02-3.93 (m, 1H), 3.17-3.04 (m, 1H), 2.68-2.57 (m, 1H); and $^{13}$CNMR (126 MHz, CDCl$_3$) 152.8, 151.0, 138.0, 135.0, 134.7, 130.4, 129.4, 129.3, 128.6, 128.1, 123.6, 115.7, 68.3, 43.1, 35.3.

Example 45 Preparation of Chiral Bicyclic Imidazole Catalyst C8

To a dry reaction flask were added (S)-6,7-dihydro-5H-pyrrolo[1,2-A]imidazol-7-ol (200 mg, 1.6 mmol, 1.0 eq) and 20 mL of tetrahydrofuran. The reaction flask was batchwise added with sodium hydride (60 wt. %, 77 mg, 1.9 mmol, 1.2 eq) at 0° C., and stirred for 30 min. Then, the reaction system was added with ethyl 2-isocyanatobenzoate (462 mg, 2.4 mmol, 1.5 eq), and reacted at 20° C. for 12 h. After that, the reaction mixture was quenched with 30 mL of water, and subjected to extraction with 30 mL of dichloromethane. The organic phases were combined, dried with magnesium sulfate anhydrous, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C8 (298 mg and 59% yield).

$^1$HNMR (500 MHz, CDCl$_3$) δ10.60 (s, 1H), 8.47 (d, J=8.5 Hz, 1H), 8.01 (dd, J=8.1, 1.6 Hz, 1H), 7.59-7.50 (m, 1H), 7.21 (s, 1H), 7.04 (t, J=7.6 Hz, 1H), 6.97 (s, 1H), 6.07 (d, J=6.3 Hz, 1H), 4.39-4.29 (m, 2H), 4.25-4.17 (m, 1H), 4.06-3.98 (m, 1H), 3.13-3.03 (m, 1H), 2.74-2.66 (m, 1H), 1.38 (t, J=7.1 Hz, 3H); and $^{13}$CNMR (126 MHz, CDCl$_3$) δ168.0, 152.7, 141.4, 134.5, 130.8, 121.7, 118.9, 115.5, 115.0, 67.8, 61.3, 43.0, 35.1, 14.2.

Example 46 Preparation of Chiral Bicyclic Imidazole Catalyst C9

To a dry reaction flask were added (S)-6,7-dihydro-5H-pyrrolo[1,2-A]imidazol-7-ol (300 mg, 2.4 mmol, 1.0 eq) and 20 mL of dichloromethane and triethylamine (1.68 mL, 12.1 mmol, 5.0 eq) followed by stirring for 5 min. The reaction flask was added with diisopropylcarbamoyl chloride (415 mg, 2.5 mmol, 1.05 eq), and reacted at 20° C. for 12 h. After that, the reaction mixture was quenched with 30 mL of water, and subjected to extraction with 30 mL of dichloromethane. The organic phases were combined, dried with magnesium sulfate anhydrous, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C9 (161 mg and 27% yield).

$^1$HNMR (500 MHz, CDCl$_3$) δ7.19 (d, J=1.2 Hz, 1H), 6.95 (d, J=1.3 Hz, 1H), 5.96 (dd, J=7.1, 2.8 Hz, 1H), 4.18-4.11 (m, 1H), 4.09-3.95 (m, 2H), 3.76 (s, 1H), 3.12-3.03 (m, 1H), 2.64-2.56 (m, 1H), 1.19 (s, 12H);

$^{13}$CNMR (126 MHz, CDCl$_3$) δ154.8, 151.9, 134.7, 115.3, 67.6, 46.6, 45.7, 43.0, 35.7, 21.5, 20.6.

Example 47 Preparation of Chiral Bicyclic Imidazole Catalyst C10

To a dry reaction flask were added (S)-6,7-dihydro-5H-pyrrolo[1,2-A]imidazol-7-ol (300 mg, 2.4 mmol, 1.0 eq) and 20 mL of dichloromethane and triethylamine (1.68 mL, 12.1 mmol, 5.0 eq) followed by stirring for 5 min. The reaction mixture was added with 1-piperidinecarbonyl chloride (0.32 mL, 2.5 mmol, 1.05 eq), and reacted at 20° C. for 12 h. After that, the reaction mixture was quenched with 30 mL of water, and subjected to extraction with 30 mL of dichloromethane. The organic phases were combined, dried with magnesium sulfate anhydrous, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C10 (271 mg and 48% yield).

$^1$HNMR (500 MHz, CDCl$_3$) δ7.19 (d, J=1.2 Hz, 1H), 6.95 (d, J=1.2 Hz, 1H), 5.91 (dd, J=7.3, 2.9 Hz, 1H), 4.20-4.11 (m, 1H), 4.01-3.93 (m, 1H), 3.47-3.32 (m, 4H), 3.14-3.03 (m, 1H), 2.65-2.55 (m, 1H), 1.61-1.45 (m, 6H); and $^{13}$CNMR (126 MHz, CDCl$_3$) δ154.7, 151.7, 134.6, 115.3, 68.1, 44.9, 42.9, 35.4, 25.6, 24.3.

Example 48 Preparation of Chiral Bicyclic Imidazole Catalyst C11

To a dry reaction flask were added (S)-6,7-dihydro-5H-pyrrolo[1,2-A]imidazol-7-ol (300 mg, 2.4 mmol, 1.0 eq) and 30 mL of tetrahydrofuran. The reaction flask was batchwise added with sodium hydride (60 wt. %, 116 mg, 2.9 mmol, 1.2 eq) at 0° C. and stirred for 30 min. Then, the reaction mixture was added with tert-butyl isocyanate (0.43 mL, 3.6 mmol, 1.5 eq), and reacted at 20° C. for 12 h. After that, the reaction mixture was quenched with 30 mL of water, and subjected to extraction with 30 mL of dichloromethane. The organic phases were combined, dried with magnesium sulfate anhydrous, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C11 (460 mg and 85% yield).

$^1$HNMR (500 MHz, CDCl$_3$) δ7.18 (s, 1H), 6.94 (s, 1H), 5.88 (dd, J=7.4, 2.7 Hz, 1H), 4.78 (s, 1H), 4.19-4.09 (m, 1H), 4.05-3.93 (m, 1H), 3.14-3.00 (m, 1H), 2.68-2.54 (m, 1H), 1.32 (s, 9H); and $^{13}$CNMR (126 MHz, CDCl$_3$) δ155.0, 151.7, 134.9, 115.5, 67.2, 50.7, 43.1, 35.5, 29.0.

Example 49 Preparation of Chiral Bicyclic Imidazole Catalyst C12

To a dry reaction flask were added (S)-6,7-dihydro-5H-pyrrolo[1,2-A]imidazol-7-ol (300 mg, 2.4 mmol, 1.0 eq) and 30 mL of tetrahydrofuran. The reaction flask was batchwise added with sodium hydride (60 wt. %, 116 mg, 2.9 mmol, 1.2 eq) at 0° C., and stirred for 30 min. Then, the reaction mixture was added with 3-isopropenyl-alpha (0.72 mL, 3.6 mmol, 1.5 eq), and reacted at 20° C. for 12 h. After that, the reaction mixture was quenched with 30 mL of water, and subjected to extraction with 30 mL of dichloromethane. The organic phases were combined, dried with magnesium sulfate anhydrous, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst (415 mg and 53% yield).
$^1$HNMR (400 MHz, CDCl$_3$) δ7.48 (s, 1H), 7.36-7.27 (m, 3H), 7.18 (s, 1H), 6.94 (s, 1H), 5.82 (dd, J=7.4, 2.8 Hz, 1H), 5.38-5.25 (m, 2H), 5.11-5.05 (m, 1H), 4.17-4.07 (m, 1H), 3.99-3.89 (m, 1H), 3.08-2.95 (m, 1H), 2.62-2.49 (m, 1H), 2.15 (s, 3H), 1.70 (s, 3H), 1.66 (s, 3H); and
$^{13}$CNMR (101 MHz, CDCl$_3$) δ153.7, 151.4, 146.7, 143.5, 141.3, 134.7, 128.3, 124.1, 124.0, 122.0, 115.4, 112.6, 67.4, 55.4, 42.9, 35.4, 29.5, 28.9, 22.0.

Example 50 Preparation of Chiral Bicyclic Imidazole Catalyst C13

To a dry reaction flask A were added triphosgene (474.8 mg, 1.6 mmol, 1.0 eq) and 10 mL of dichloromethane. A dropping funnel was added with tert-octylamine (0.48 mL, 1.6 mmol, 1.0 eq) and 3 mL of a dichloromethane. A dichloromethane solution of tert-octylamine was added dropwise to a dichloromethane solution of triphosgene at 0° C. 10 min later, triethylamine (0.89 mL, 6.4 mmol, 4.0 eq) and 3 mL of dichloromethane were added to the dropping funnel, and then added to the above reaction solution, and reacted at 20° C. for 2 h. A dry reaction flask B was added with (S)-6,7-dihydro-5H-pyrrolo[1,2-A]imidazol-7-ol (200 mg, 1.6 mmol, 1.0 eq) and 20 mL of tetrahydrofuran. The reaction mixture was added with sodium hydride (60 wt. %, 193 mg, 4.8 mmol, 3.0 eq) at 0° C., and stirred for 30 min. Then, the solution in the dry reaction flask A was transferred to the dry reaction flask B, and reacted for 12 h at 20° C. After that, the reaction mixture was quenched with 30 mL of water, and subjected to extraction with 30 mL of dichloromethane. The organic phases were combined, dried with magnesium sulfate anhydrous, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C13 (164.8 mg and 43% yield).
$^1$HNMR (400 MHz, CDCl$_3$) δ7.19 (d, J=1.3 Hz, 1H), 6.95 (d, J=1.2 Hz, 1H), 5.86 (dd, J=7.4, 2.7 Hz, 1H), 4.75 (s, 1H), 4.19-4.08 (m, 1H), 4.03-3.92 (m, 1H), 3.14-3.01 (m, 1H), 2.64-2.52 (m, 1H), 1.79 (d, J=14.9 Hz, 1H), 1.59 (d, J=14.9 Hz, 1H), 1.38 (s, 3H), 1.34 (s, 3H), 0.99 (s, 9H); and
$^{13}$CNMR (101 MHz, CDCl$_3$) δ153.7, 151.7, 134.7, 115.5, 67.3, 54.4, 51.7, 43.1, 35.7, 31.7, 31.6, 29.5, 29.5.

Example 51 Preparation of Chiral Bicyclic Imidazole Catalyst C14

To a dry reaction flask were added (S)-6,7-dihydro-5H-pyrrolo[1,2-A]imidazol-7-ol (200 mg, 1.6 mmol, 1.0 eq) and 20 mL of tetrahydrofuran. The reaction flask was batchwise added with sodium hydride (60 wt. %, 77 mg, 1.9 mmol, 1.2 eq)) at 0° C., and stirred for 30 min. Then, the reaction mixture was added with isopropyl isocyanate (0.18 mL, 2.4 mmol, 1.5 eq), and reacted at 20° C. for 12 h. After that, the reaction mixture was quenched with 30 mL of water, and subjected to extraction with 30 mL of dichloromethane. The organic phases were combined, dried with magnesium sulfate anhydrous, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C14 (158 mg and 47% yield).
$^1$HNMR (500 MHz, CDCl$_3$) δ7.19 (s, 1H), 6.95 (s, 1H), 5.91 (dd, J=7.2, 2.7 Hz, 1H), 4.63 (d, J=7.3 Hz, 1H), 4.18-4.10 (m, 1H), 4.01-3.94 (m, 1H), 3.89-3.78 (m, 1H), 3.12-3.02 (m, 1H), 2.66-2.56 (m, 1H), 1.15 (d, J=6.4 Hz, 6H); and
$^{13}$CNMR (126 MHz, CDCl$_3$) δ154.7, 151.5, 134.8, 115.4, 67.5, 43.2, 42.9, 35.3, 23.0.

Example 52 Preparation of Chiral Bicyclic Imidazole Catalyst C15

To a dry reaction flask were added (S)-6,7-dihydro-5H-pyrrolo[1,2-A]imidazol-7-ol (200 mg, 1.6 mmol, 1.0 eq) and 20 mL of tetrahydrofuran. The reaction flask was batchwise added with sodium hydride (60 wt. %, 77 mg, 1.9 mmol, 1.2 eq) at 0° C., and stirred for 30 min. Then, the reaction mixture was added with 1-adamantyl isocyanate (428 mg, 2.4 mmol, 1.5 eq), and reacted at 20° C. for 12 h. After that, the reaction mixture was quenched with 30 mL of water, and subjected to extraction with 30 mL of dichloromethane. The organic phases were combined, dried with magnesium sulfate anhydrous, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C15 (285 mg and 59% yield).
$^1$HNMR (500 MHz, CDCl$_3$) δ7.18 (d, J=1.3 Hz, 1H), 6.94 (d, J=1.2 Hz, 1H), 5.86 (dd, J=7.2, 2.7 Hz, 1H), 4.72 (s, 1H), 4.19-4.06 (m, 1H), 4.03-3.91 (m, 1H), 3.11-2.98 (m, 1H), 2.66-2.53 (m, 1H), 2.11-2.05 (m, 3H), 1.95-1.90 (m, 6H), 1.68-1.64 (m, 6H);
$^{13}$CNMR (126 MHz, CDCl$_3$) δ153.5, 151.7, 134.8, 115.5, 67.1, 51.0, 43.1, 42.6, 41.8, 36.6, 36.3, 35.4, 29.7, 29.5.

Example 53 Preparation of Chiral Bicyclic Imidazole Catalyst C16

To a dry reaction flask were added a bicyclic imidazole C7 (319 mg, 1.0 mmol, 1.0 eq) and 10 mL of tetrahydrofuran. The reaction flask was batchwise added with sodium hydride (60 wt. %, 48 mg, 1.2 mmol, 1.2 eq) at 0° C., and stirred for 30 min. Then, the reaction mixture was added with iodomethane (62.3 μL, 1.0 mmol, 1.0 eq), and reacted at 20° C. for 12 h. After that, the reaction mixture was quenched with 20 mL of water, and subjected to extraction with 20 mL of dichloromethane. The organic phases were combined, dried with magnesium sulfate anhydrous, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C16 (185 mg and 55% yield).
$^1$HNMR (500 MHz, CDCl$_3$) δ7.47-7.19 (m, 20H), 7.17-7.12 (m, 1H), 6.93-6.88 (m, 1H), 5.93-5.80 (m, 2H), 4.19-3.80 (m, 4H), 3.08 (s, 3H), 2.98-2.80 (m, 5H), 2.46-2.36 (m, 1H), 2.00-1.91 (m, 1H); and $^{13}$CNMR (126 MHz, CDCl$_3$) δ174.0, 154.6, 151.1, 150.9, 140.8, 139.9, 139.8, 139.6, 138.9, 134.1, 133.8, 133.6, 130.9, 130.6, 128.5, 128.4, 128.3, 128.3, 128.2, 127.8, 127.6, 127.3, 115.6, 115.4, 115.3, 68.2, 68.1, 43.3, 43.0, 38.3, 37.7, 35.6, 34.6, 21.4.

Example 54 Preparation of Chiral Bicyclic Imidazole Catalyst C17

To a dry reaction flask were added a bicyclic imidazole C11 (223 mg, 1.0 mmol, 1.0 eq) and 10 mL of tetrahydrofuran. The reaction flask was batchwise added with sodium hydride (60 wt. %, 48 mg, 1.2 mmol, 1.2 eq) at 0° C., and stirred for 30 min. Then, the reaction mixture was added with iodomethane (62.3 μL, 1.0 mmol, 1.0 eq), and reacted at 20° C. for 12 h. After that, the reaction mixture was quenched with 20 mL of water, and subjected to extraction with 20 mL of dichloromethane. The organic phases were combined, dried with magnesium sulfate anhydrous, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C17 (193 mg and 81% yield).

$^1$HNMR (400 MHz, CDCl$_3$) δ7.19 (d, J=1.2 Hz, 1H), 6.95 (d, J=1.2 Hz, 1H), 5.91 (dd, J=7.2, 2.8 Hz, 1H), 4.19-4.10 (m, 1H), 4.02-3.93 (m, 1H), 3.13-3.02 (m, 1H), 2.88 (s, 3H), 2.63-2.54 (m, 1H), 1.38 (s, 9H); and $^{13}$CNMR (101 MHz, CDCl$_3$) δ155.6, 151.9, 134.6, 115.4, 67.7, 55.9, 43.0, 35.6, 31.5, 28.7.

Example 55 Preparation of Chiral Bicyclic Imidazole Catalyst C18

To a dry reaction flask were added (S)-6,7-dihydro-5H-pyrrolo[1,2-A]imidazol-7-ol (200 mg, 1.6 mmol, 1.0 eq) and 10 mL of dichloromethane and 2,6-lutidine (0.56 mL, 4.8 mmol, 3.0 eq) followed by stirring for 5 min. The reaction flask was added with trifluoromethanesulfonic acid tert-butyldimethylsilyl ester (0.74 mL, 3.2 mmol, 2.0 eq) at 0° C., reacted at 20° C. for 24 h, and subjected to rotary evaporation and silica-gel column chromatography (particle size: 100~200 mesh; specific surface area: 300-400 m$^2$/g; and mobile phase: ethyl acetate) to obtain the chiral bicyclic imidazole catalyst C18 (287 mg and 75% yield).

$^1$HNMR (500 MHz, CDCl$_3$) δ7.13 (d, J=1.3 Hz, 1H), 6.85 (d, J=1.2 Hz, 1H), 5.10 (dd, J=6.8, 2.9 Hz, 1H), 4.18-4.11 (m, 1H), 3.91-3.83 (m, 1H), 2.90-2.79 (m, 1H), 2.50-2.42 (m, 1H), 0.92 (s, 9H), 0.21 (s, 3H), 0.13 (s, 3H); and $^{13}$CNMR (126 MHz, CDCl$_3$) δ155.0, 134.0, 114.6, 66.3, 42.8, 38.3, 25.9, 18.4, −4.6, −4.8.

Described above are merely preferred embodiments of this application, which are not intended to limit the scope of the application. It should be understood by those skilled in the art that any changes, and modifications made without departing from the spirit shall fall within the scope of the present application defined by the appended claims.

What is claimed is:

1. A method for preparing a phosphorus-stereogenic (P-stereogenic) nucleoside derivative of formula (3), comprising:

subjecting a nucleoside and phosphoryl chloride to asymmetric reaction in a solvent under the catalysis of a chiral bicyclic imidazole catalyst in the presence of a base to obtain the P-stereogenic nucleoside derivative of formula (3):

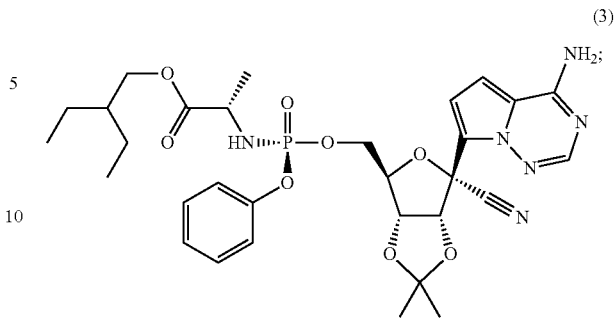

(3)

wherein the base is an inorganic base, and the inorganic base is selected from the group consisting of sodium carbonate, potassium carbonate, cesium carbonate, disodium hydrogen phosphate, sodium bicarbonate and potassium bicarbonate.

2. The method of claim 1, wherein the chiral bicyclic imidazole catalyst is selected from the group consisting of:

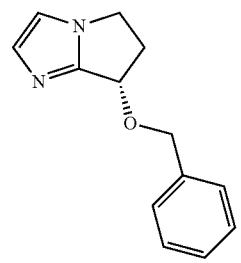

C1

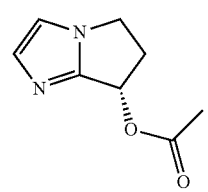

C2

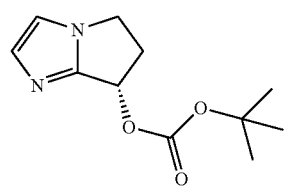

C3

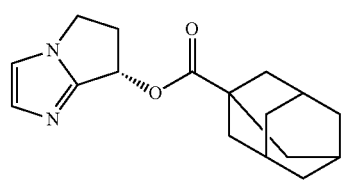

C4

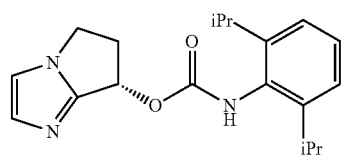

C5

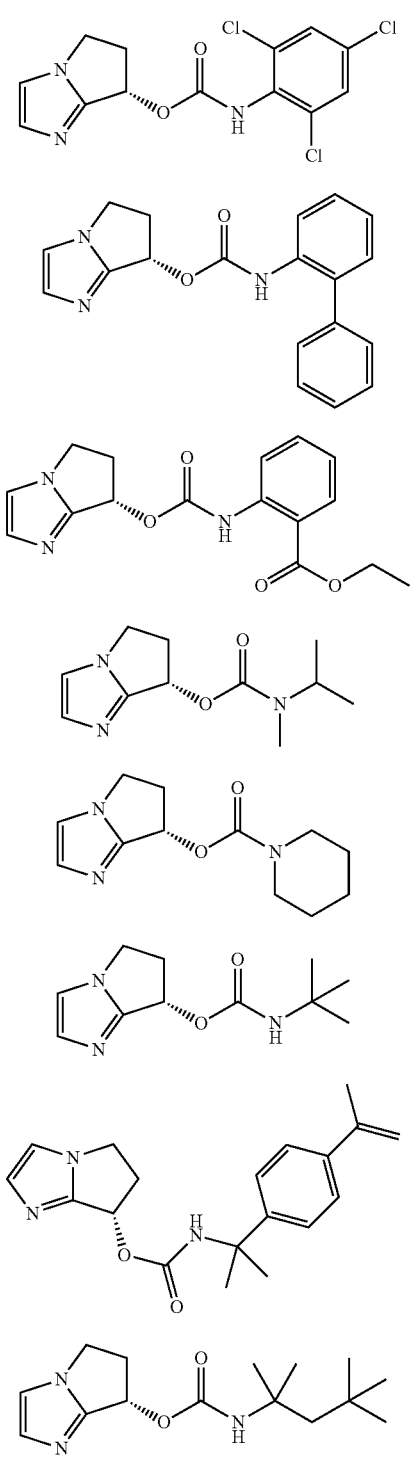
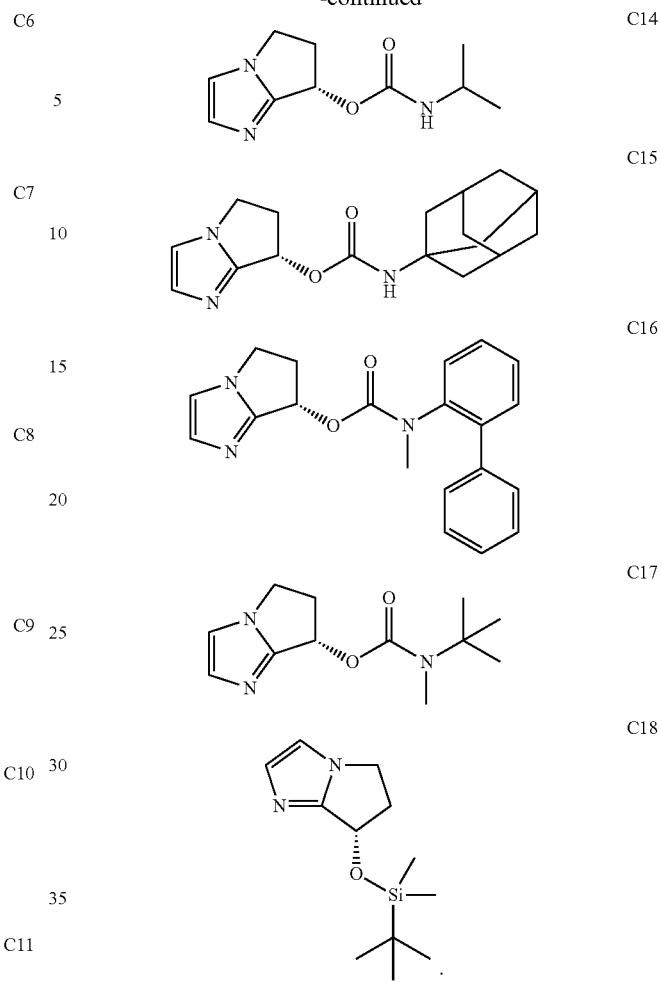

3. The method of claim 2, wherein C1-C18 are all in S configuration.

4. The method of claim 1, wherein the solvent is selected from the group consisting of methylbenzene, diethyl ether, 1,3-dioxolane, 1,4-dioxane, tetrahydrofuran, dichloromethane, trichloromethane, 1,2-dichloroethane, ethyl acetate, acetone, acetonitrile and a combination thereof.

5. The method of claim 1, wherein a molar ratio of the chiral bicyclic imidazole catalyst to the nucleoside is 1:(5~100).

6. The method of claim 1, wherein a molar ratio of the nucleoside to the phosphoryl chloride is 1:(0.5~3.0); and a molar ratio of the nucleoside to the base is 1:(1.0~4.0).

7. The method of claim 1, wherein the asymmetric reaction is performed at −100~80° C. for 1-72 h.

* * * * *